United States Patent
Wolf et al.

(10) Patent No.: US 7,072,717 B1
(45) Date of Patent: Jul. 4, 2006

(54) MULTIRATE COCHLEAR STIMULATION STRATEGY AND APPARATUS

(75) Inventors: Joe Wolf, Coogee (AU); Paul Michael Carter, Carlingford (AU); Simon Geoffrey Parker, Ryde (AU); Robert Fearn, Maroubra (AU); Niki Frampton, Eastwood (AU)

(73) Assignee: Cochlear Limited, Lane Cove (AU)

( * ) Notice: Subject to any disclaimer, the term of this patent is extended or adjusted under 35 U.S.C. 154(b) by 618 days.

(21) Appl. No.: 10/030,830

(22) PCT Filed: Jul. 13, 2000

(86) PCT No.: PCT/AU00/00838

§ 371 (c)(1),
(2), (4) Date: Jun. 5, 2002

(87) PCT Pub. No.: WO01/03622

PCT Pub. Date: Jan. 18, 2001

(30) Foreign Application Priority Data

Jul. 13, 1999 (AU) .................................... PQ1610

(51) Int. Cl.
A61F 11/04 (2006.01)
H04R 25/00 (2006.01)
(52) U.S. Cl. ........................................ 607/57; 381/320
(58) Field of Classification Search ............ 607/55–57, 607/136, 137
See application file for complete search history.

(56) References Cited

U.S. PATENT DOCUMENTS

| | | | |
|---|---|---|---|
| 4,357,497 A | 11/1982 | Hochmair et al. | |
| 4,400,590 A | 8/1983 | Michelson | |
| 4,441,202 A * | 4/1984 | Tong et al. | 381/326 |
| 4,532,930 A | 8/1985 | Crosby et al. | |
| 4,593,696 A * | 6/1986 | Hochmair et al. | 607/57 |
| 5,597,380 A * | 1/1997 | McDermott et al. | 607/57 |
| 5,601,617 A | 2/1997 | Loeb et al. | |
| 5,749,912 A | 5/1998 | Zhang et al. | |
| 5,800,475 A | 9/1998 | Jules | |
| 6,289,247 B1 * | 9/2001 | Faltys et al. | 607/57 |

OTHER PUBLICATIONS

PCT International Search Report for PCT/AU00/00838; filed Jul. 13, 2000; published Jan. 18, 2001 (WO 01/03622 A1).

Technical Manual: The Laura Cochlear Prosthesis, Antwerp Bionic Systems, N.V., 1991.

Peeters, et al., The Laura Cochlear Implant Programmed with the Continuous Interleaved and Phase-Locked Continuous Interleaved Strategies, Cochlear Implants: New Perspectives, 1993.

Kong, Lai Wai, Psychophysical Studies Investigating a Place/Rate Speech Coding Strategy for a Multi-Electrode Cochlear Implant, University of Melbourne, Thesis, Jul. 1990.

* cited by examiner

*Primary Examiner*—George Manuel
*Assistant Examiner*—Nicole R. Kramer
(74) *Attorney, Agent, or Firm*—Jagtiani + Guttag

(57) ABSTRACT

An improved processing approach is disclosed in order to allow for different rates of stimulation to be used for different electrodes in a multi-electrode cochlear implant. When the incoming signal is processed by filter array (35), each channel is processed to determine amplitude (37) and to estimate the period of the signal in that channel (39). The amplitude and period information is used to determine which electrode is stimulated, and the timing of that stimulation.

18 Claims, 6 Drawing Sheets

MULTIRATE COCHLEAR STIMULATION STRATEGY AND APPARATUS

TECHNICAL FIELD

The present invention relates to cochlear implant prostheses and in particular to an apparatus and method for applying stimulation to the neural structures of a cochlea in order to improve a subject's pitch and speech perception.

BACKGROUND ART

Cochlear implant systems are used to aid patients having a hearing deficiency. More particularly, these systems include a microphone receiving ambient sounds and converting the sounds into corresponding electrical signals, signal processing means for processing the electrical signals and generating cochlear stimulating signals and an electrode assembly for applying the cochlea stimulating signals to the cochlea of an implantee. In response to these electrical stimulations a perception of corresponding ambient sound is elicited in the implantee.

The inner ear of a normally hearing person includes hair cells which convert the displacement of the ear's basilar membrane in response to sound into nervous impulses. Different parts of the basilar membrane of the normal cochlea are displaced maximally by different frequencies of sound so that low frequency sounds maximally displace apical portions whereas higher frequency sounds cause displacement of more basal portions of the membrane. The nervous system is arranged so that a nervous impulse originating from a hair cell located adjacent an apical area of the membrane is perceived as a low frequency sound whereas a nervous impulse originating from a hair cell located adjacent a more basal position of the membrane is perceived as a higher frequency sound. This mapping of position to pitch is well known in the art as the tonotopic arrangement of the cochlea.

In a dysfunctional ear the hair cells may be damaged or absent so that no nervous impulses are generated. In such cases electrical stimulation impulses must be provided artificially to simulate the nervous activity of the hair cells in order to create a perception of sound.

With reference to FIG. 1, a typical cochlear implant is shown, which consists of an external component including a speech processor 1, and an internal component including an implanted receiver and stimulator unit 6 and an intracochlear array 10. The external component further includes a microphone 2 which is shown integral with the speech processor 1. In this illustration the speech processor is arranged so that it can fit behind the ear with the microphone integral therewith. Alternative versions are also envisaged whereby the speech processor is worn on the body and separately attached to the microphone, and also where the speech processor and microphone are implanted in the patient. The present invention is applicable to all these alternatives.

In such cochlear implant devices, ambient sounds are detected by a microphone and a transduced signal is thereby generated, representative of the ambient sound. A processor unit then processes this transduced signal according to one of many strategies, (some of which will be explained further below) and based on this processing stimulation currents are applied between the electrodes of a coupled array. For example, in "monopolar" mode stimulation, stimulation currents may be caused to flow between an electrode of the electrode array 10 and an extracochlear electrode 115. Nervous discharges elicited in the basilar membrane 8 are conveyed to the central nervous system of the wearer by auditory nerve 9.

In the event that the stimulation current flows between an apical electrode such as electrode 111 and extracochlear electrode 115 then a lower pitched hearing sensation will be perceived by a wearer of the prosthesis than will be the case if stimulation current flows between basal electrode 107 and extracochlear electrode 115 because of the previously mentioned tonotopic arrangement of the cochlea. Further pitch information may be transmitted to the wearer corresponding to the rate at which stimulations are delivered.

Many possibilities exist as to the manner in which the signal processing means operates upon the electrical signals in order to produce stimulation signals. However it has been noted in the past that simultaneous stimulation of electrodes is not generally conducive to eliciting a perception of sound that is faithful to the actual acoustic signals being processed. This is because if electrodes are stimulated simultaneously, current paths between electrodes can interact, causing undesirable stimulation. Consequently most cochlear prosthesis stimulation strategies stimulate by means of only one electrode at a time.

In the past designers of cochlear implant stimulation strategies have striven to optimise the intelligibility of spoken words as perceived by the wearer of a cochlear implant.

One of the earliest sound processing and cochlear stimulation strategies is described in U.S. Pat. No. 4,532,930 to the present applicant. In that patent there is taught the use of a filter (F0) dedicated to extracting the voice pitch of a speech signal. The periodicity of the voice pitch is used to set the stimulation periodicity for two or three electrodes. A second, and possibly third, channel is analysed to determine periodicity and amplitude in a selected frequency band.

The periodicity extracted from the second filter, and possibly third filter, is used to select which electrode is stimulated for the second and third channels while the periodicity of stimulation of the channel is determined by the periodicity of the output signal from the F0 filter.

Another stimulation arrangement is described in U.S. Pat. No. 4,207,441. In that system there are n electrodes each coupled to one of n filters. Each electrode is stimulated once per analysis period, with an intensity corresponding to the amplitude of the corresponding filter channel. The analysis period of this system is predetermined and hence is not related to the signal on the filter outputs.

More recently in EP 0 745 363 there is described a stimulation system which takes into account the temporal behaviour of the cochlea. In an embodiment of the invention therein described a wavelet transformation is used to extract the temporal information with a view to using this information to determine the sequence of stimulation of the electrodes. The purpose of the invention is to improve the temporal resolution in response to a rapidly changing audio spectrum.

A problem that has been faced by users of cochlear implants featuring prior art stimulation schemes is that while intelligibility of spoken words is often good the user's pitch perception, and in particular perception of music, is poor. Accordingly, it is an object of the present invention to provide an apparatus and method for use in a multi-channel cochlear implant which will improve a user's perception of pitch.

SUMMARY OF THE INVENTION

Broadly, the present invention seeks to use information about the periodicity of the signal in each filter channel as a factor in determining the rate of stimulation applied to a tonotopically placed electrode which corresponds to the relevant channel. This allows for an improved perception of pitch by the implant user. As a result, the rate of stimulation which occurs in practice for each electrode will be related to the periodicity of the signal in the filter channel corresponding to that electrode.

According to one aspect of the present invention there is provided a cochlear implant prosthesis of the type having a transducer for converting an acoustic signal to an electrical signal, a plurality of bandpass filtering means responsive to said electrical signal and operatively producing a plurality of bandpass filtered signals, signal processing means responsive to said plurality of bandpass filtered signals and operatively generating stimulation commands, electrode driving means responsive to said stimulation commands and an electrode array coupled to said electrode driving means for operatively delivering to a user of said cochlear implant prosthesis stimulations in accordance with said stimulation commands, said signal processing means including:

a) period estimation means, responsive to said filtered signals and operatively generating periodicity signals indicative of the periodicity of each of at least a number of said plurality of filtered signals;

b) amplitude estimation means responsive to said filtered signals and operatively generating magnitude signals indicative of the magnitude of each of said plurality of filtered signals;

c) selection means responsive to said magnitude signals arranged to select only one filtered signal of said plurality of filtered signals in each stimulation period, said selection means generating said stimulation commands including a command to stimulate by means of an electrode operatively tonotopically best corresponding to said one filtered signal, said command to stimulate further specifying a time for stimulation to occur dependent on a corresponding one of said periodicity signals.

According to another aspect, the present invention provides a processing device for a cochlear implant prosthesis, said prosthesis being of the type including electrode driving means responsive to stimulation commands and an electrode array coupled to said electrode driving means for operatively delivering to a user of said cochlear implant prosthesis stimulations in accordance with said stimulation commands, said processing device being responsive to a transducer for converting an acoustic signal to an electrical signal and including a plurality of bandpass filtering means responsive to said electrical signal and operatively producing a plurality of bandpass filtered signals, signal processing means responsive to said plurality of bandpass filtered signals and operatively generating stimulation commands, said signal processing means including:

a) period estimation means, responsive to said filtered signals and operatively generating periodicity signals indicative of the periodicity of each of at least a number of said plurality of filtered signals;

b) amplitude estimation means responsive to said bandpass filters operatively generating magnitude signals indicative of the magnitude of each of said plurality of filtered signals;

c) selection means responsive to said magnitude signals arranged to select only one filtered signal of said plurality of filtered signals in each stimulation period, said selection means generating said stimulation commands including a command to stimulate by means of an electrode operatively tonotopically best corresponding to said filtered signal, said command to stimulate further specifying a time for stimulation to occur dependent on a corresponding one of said periodicity signals.

According to a further aspect of the present invention there is provided a method of operating a cochlear implant prosthesis of the type including a plurality of bandpass filters each having a characteristic centre frequency, said filters generating a corresponding plurality of filtered signals, said prosthesis further including stimulation delivery means coupled to an electrode array, said method including the steps of:

a) in each of a number of time intervals, determining the amplitude for each of said plurality of filtered signals and a periodicity value for at least some of said plurality of filtered signals;

b) selecting only one of said signals as a basis for stimulation in each stimulation period; and c) applying a stimulation current by means of an electrode of said electrode array tonotopically closest to the centre frequency of the bandpass filter producing the signal determined in step b), said stimulation current being applied during a time interval determined from the periodicity value of the signal determined in step b).

DETAILED DESCRIPTION

The present invention will be described with reference to a specific implementation. However, it will be appreciated that the present invention can be implemented in various ways, with suitable modifications to suit the cochlear implant system in question.

Figure 1:
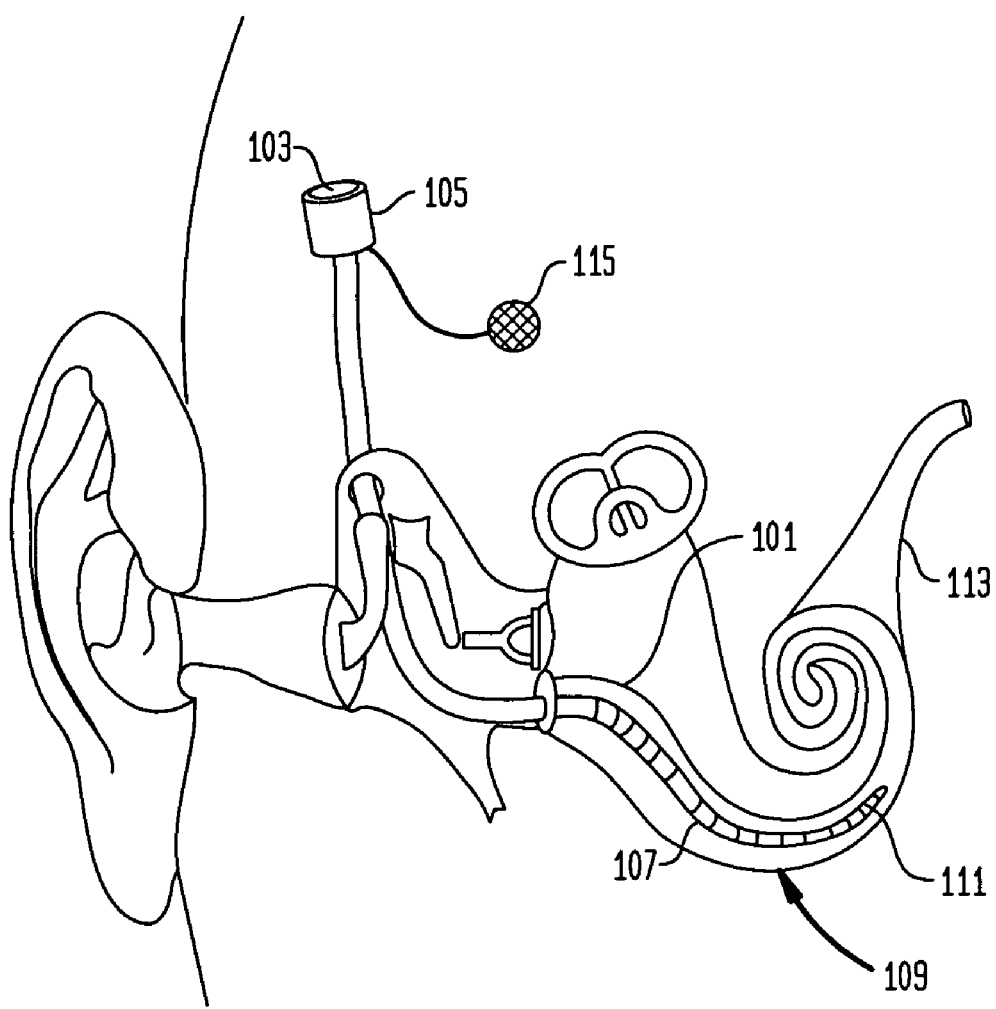
FIG. 1 depicts a typical cochlear implant device.
Figure 1A:
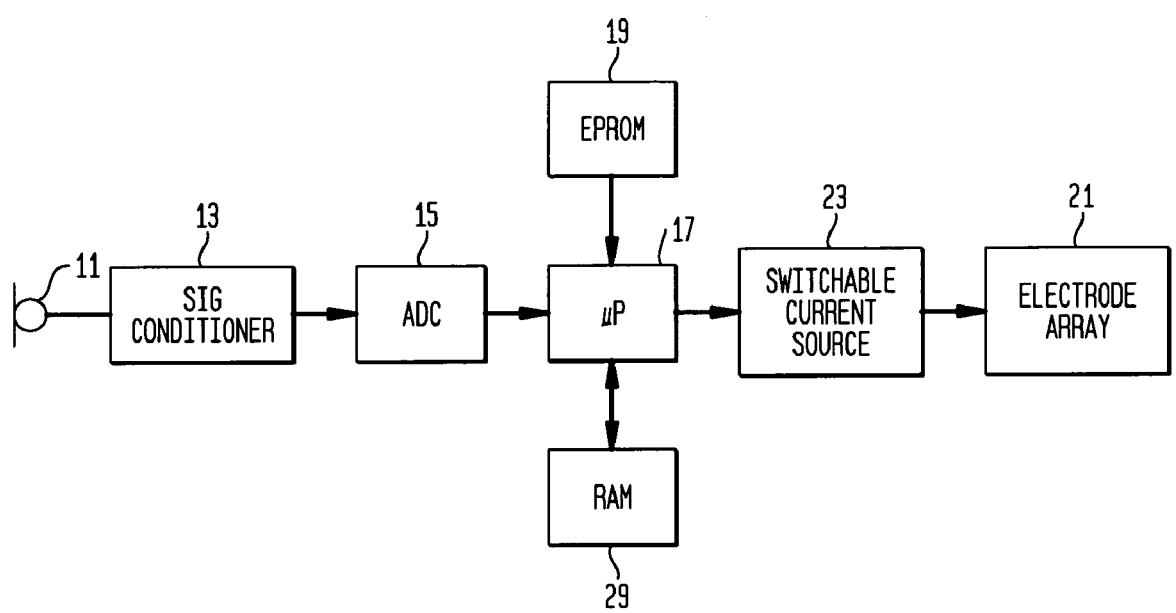
FIG. 1A depicts a block diagram of the functional elements of a cochlear implant according to the present invention.

With reference to FIG. 1A, there is depicted a simplified digital hardware implementation of a cochlear prosthesis according to the present invention. Sound waves are transduced by microphone 11 and the electrical signal so produced is processed by a signal conditioning module 13.

Signal conditioning module 13 includes standard circuits for pre-amplifying and low pass filtering the signal prior to its processing by analog to digital converter 15. Analog to digital converter 15 produces a 16 bit digital signal which is conveyed to microprocessor 17. Microprocessor 17 operates according to a program stored in EPROM 19. Microprocessor 17, in accordance with its program operates upon the digital signal in order to generate a sequence of stimulation commands which are delivered to a switchable current source module 23. The commands delivered to the switchable current source module 23 specify the amplitude of the current that is to flow from one or more electrode to one or more other electrodes, the timing of the stimulation current, and the mode of the stimulation.

The term 'mode' here refers to the selection of electrodes between which a stimulation current is to flow. Well known stimulation modes include bipolar, monopolar and common ground. Upon receiving commands specifying the parameters of the stimulation to be applied, switchable current source module 23 connects various electrodes of electrode array 21 to an internal controllable current source in order to generate the appropriate stimulation. The construction of a switchable current source is well known in the art and may be found in the applicant's U.S. Pat. No. 4,532,930.

Figure 2:
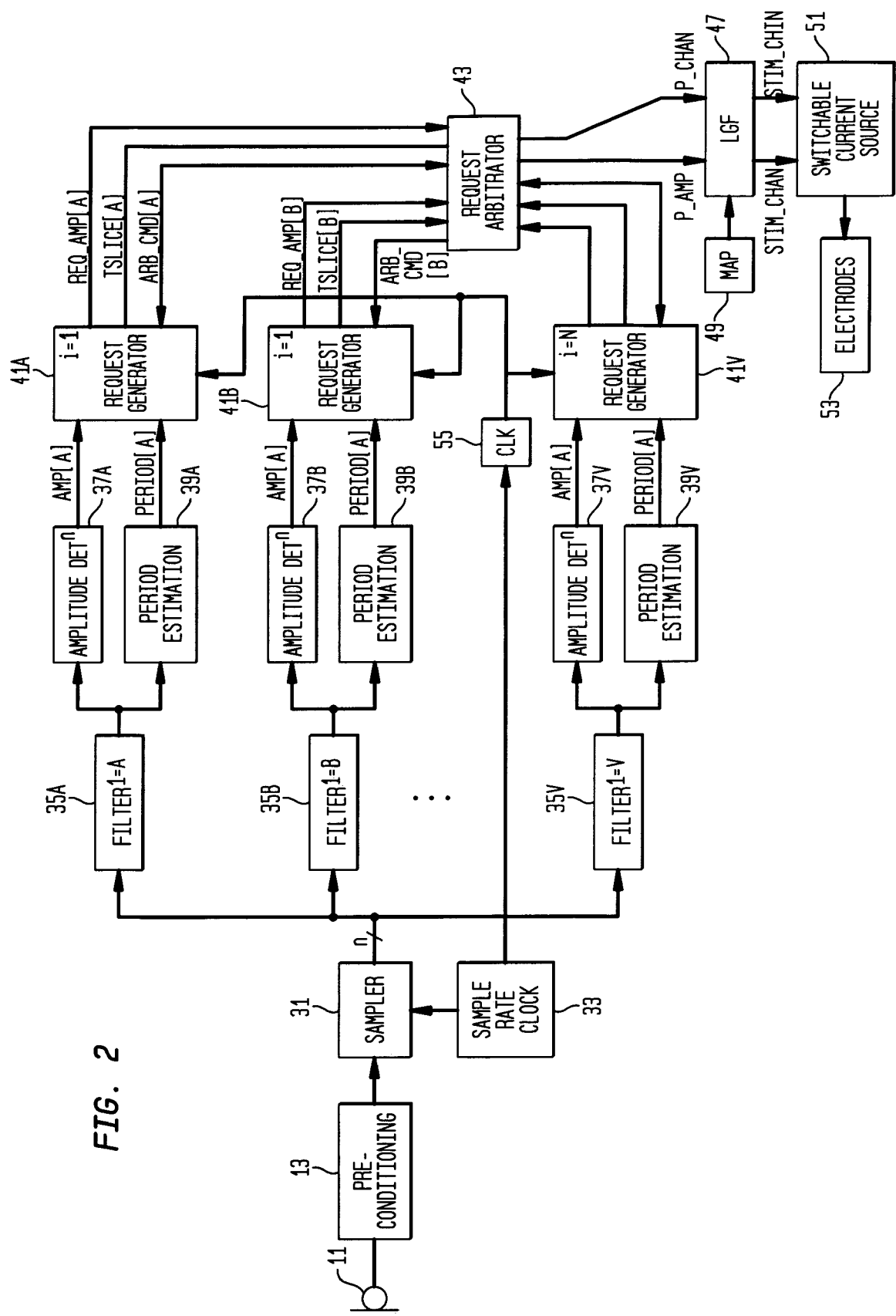
FIG. 2 depicts a dedicated hardware version of a cochlear implant prosthesis according to the present invention.

FIG. 2 depicts a dedicated hardware implementation of the invention for purposes of explanation. While FIG. 2 illustrates the invention as if individual tasks performed by microprocessor 17 were embodied in dedicated hardware, it remains the case that the invention is most readily practised according to the arrangement of FIG. 1A. The invention will however be explained with reference to FIG. 2 in order to most clearly impart an understanding of its operation to the reader.

Referring to FIG. 2 it will be noted that the analog signal from pre-conditioning module 13 is first sampled at 16 kHz by sampler 31 thereby producing a sampled signal. The sampled signal is split 22 ways, each of the split signals providing an input to digital filters 35A–35V which filter the signal into quarter octave frequency bands. It will be appreciated that the numbers of ways the signal is split, and the sampling rate, are matters of design choice appropriate to the system in which the present invention is implemented.

Digital filters 35A–35V are bandpass and logarithmically spaced with the base frequency being typically at 150 Hz. Each filter is of a 6th order Chebychev Type I bandpass type implemented in three second order sections. The quarter octave frequency bands are as shown below:

| Filter Band | Lower Frequency Boundary (Hz) | Upper Frequency Boundary (Hz) |
|---|---|---|
| A | 150.00 | 178.38 |
| B | 178.38 | 212.13 |
| C | 212.13 | 252.27 |
| D | 252.27 | 300.00 |
| E | 300.00 | 356.76 |
| F | 356.76 | 424.26 |
| G | 424.26 | 504.54 |
| H | 504.54 | 600.00 |
| I | 600.00 | 713.52 |
| J | 713.52 | 848.53 |
| K | 848.53 | 1009.10 |
| L | 1009.10 | 1200.00 |
| M | 1200.00 | 1427.00 |
| N | 1427.00 | 1697.10 |
| O | 1697.10 | 2018.20 |
| P | 2018.20 | 2400.00 |
| Q | 2400.00 | 2854.10 |

-continued

| Filter Band | Lower Frequency Boundary (Hz) | Upper Frequency Boundary (Hz) |
|---|---|---|
| R | 2854.10 | 3394.10 |
| S | 3394.10 | 4036.30 |
| T | 4036.30 | 4800.00 |
| U | 4800.00 | 5708.20 |
| V | 5708.20 | 6788.20 |

The bandpass filtered signal from each of the digital filters, for example 35A, is connected to an amplitude detection module 37A and a period estimation module 39A. The output AMP[A] of amplitude detection module 37A is a digital signal representing an estimation of the amplitude of the sampled signal from filter 35A. The construction of module 37A is straightforward, well understood by those skilled in the art, and will not be explained in detail other than to say that it could be based on a series of comparators.

Period estimation module 39A counts sampling periods between positive zero crossings of the signal from filter 35A. The output signal PERIOD[A] is scaled so that it is expressed in units of "timeslices".

Figure 3A:
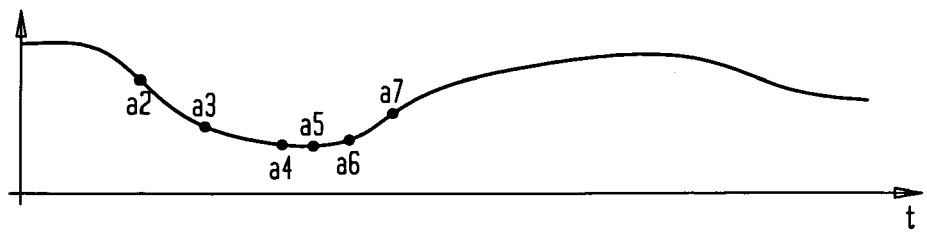
FIG. 3A is a graph of a possible output of an amplitude estimator module of FIG. 2.
Figure 3B:
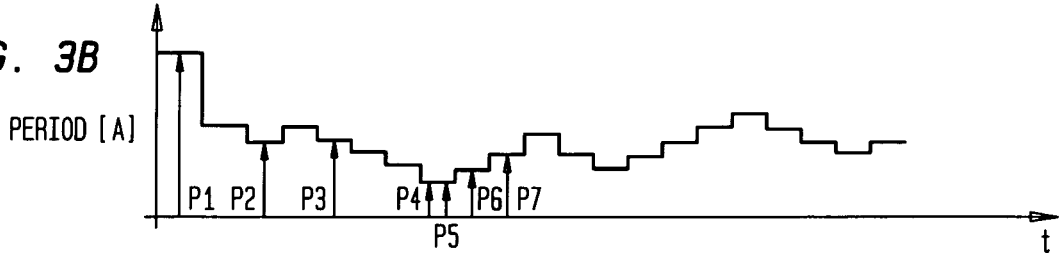
FIG. 3B is a graph of a possible output of a period estimator module of FIG. 2 of the same channel as the amplitude estimator of FIG. 3A.
Figure 3C:
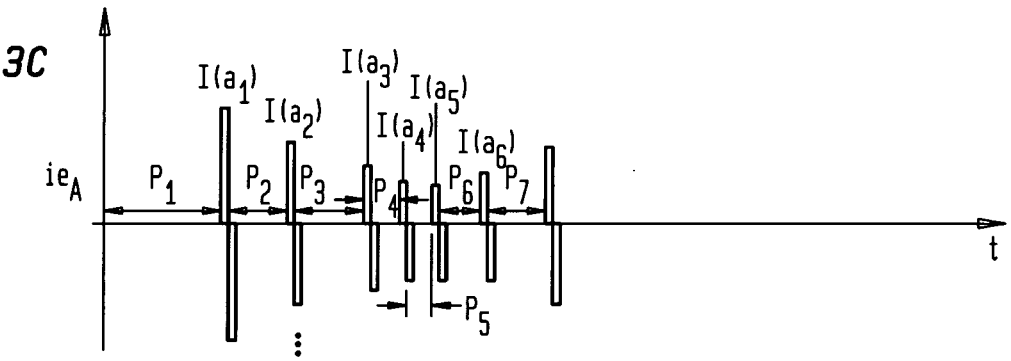
FIG. 3C is a graph of stimulation currents generated via an electrode in accordance with the amplitude and period estimates of FIGS. 3A and 3B.

One "timeslice" is the time taken to deliver one stimulation pulse by means of an electrode. With reference to FIG. 3E an example of a stimulation current pulse waveform comprises a first 'phase' 103 being a square wave of predetermined amplitude, an interphase gap 105 and a second phase 107 being a current square wave of the same magnitude and duration as the first phase but flowing in the opposite direction between an intra-cochlear electrode and (in mono-polar mode) an extra-cochlear electrode. Time periods 109 and 111 are present in which the system generating the stimulations has time to perform any necessary operations in order to configure for the next stimulation. The overall time taken to set-up, deliver and recover from application of a stimulation is one timeslice, in the present example a timeslice is of approximately 69 microseconds duration.

In the present implementation the preferred maximum stimulation rate is 8 kHz whereas the preferred sampling rate is 16 kHz. Accordingly PERIOD[A] is the number of samples occurring between positive-going zero crossings divided by two and rounded. The PERIOD[A] signal is updated at the end of each period.

The AMP[A], . . . , AMP[V] and PERIOD[A], . . . , PERIOD[V] signals contain magnitude and period information concerning the ambient sound picked up by microphone 11 for each of the frequency bands monitored by bandpass filters 35. It is possible to simply stimulate via each corresponding electrode e[i] with a current intensity corresponding to AMP[i] at a time PERIOD[i] into the future in order to convey the information generated by amplitude detectors 37 and period estimators 39 to a wearer of the cochlear prosthesis. For example, with reference to FIGS. 3A, 3B and 3C a stimulation sequence via electrode e[A] is shown corresponding to amplitude and period values generated by amplitude detection module 37A and period estimation module 39A as shown plotted in FIGS. 3A and 3B. Period[A] is equal to P1 at time t=0 and Amp[A] is equal to a1. Accordingly at a time t=P1 a stimulation current is delivered via electrode e[A] of electrical amplitude l(a1) where l( ) is a loudness growth function which maps amplitude into the dynamic range of the wearer of the prosthesis.

The period P2 and amplitude a2 values are then obtained and a further stimulation is delivered at time t=P1+P2 of amplitude l(a2). This process is repeated continuously to produce the stimulation sequence of biphasic current pulses shown in the graph of FIG. 3C. As previously mentioned, such a process could be simultaneously performed independently on all channels of the implant, (a "channel" as used here refers to a stimulation electrode, its corresponding filter and period and amplitude estimation modules).

In the system thus far described the period estimation module 39A produces a period estimate which is simply the time delay between the last two positive-going zero crossings. While this system works well, any noise on the individual period estimates will degrade the performance of the system. To prevent this, it is desirable to calculate a smoothed period estimate.

The individual period estimates constitute a number sequence which is amenable to any of the methods of smoothing known to the art of digital signal processing. The smoothing may, for example, be implemented as a simple FIR or recursive digital filter—preferably a low-pass filter. Alternatively a rank-order filter, such as a median filter may be used. A rank-order filter has the advantage that it will completely remove any single data errors from the number sequence. A smoothed period estimate is thus produced by applying the sequence of period estimates to a digital filter, and taking the output of that filter. The smoothed period estimate is then utilised by taking the most recent output from the filter and using it in place of the (unsmoothed) period estimate.

Figure 3D:
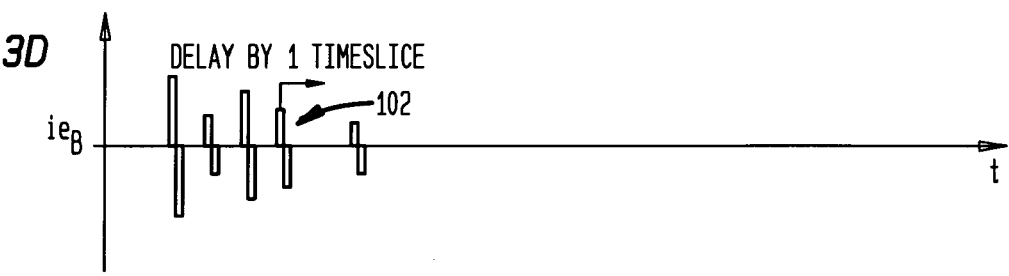
FIG. 3D is a graph of stimulation currents generated via a further electrode having a stimulation current occurring simultaneously with a stimulation current in the graph of FIG. 3C.
Figure 3E:
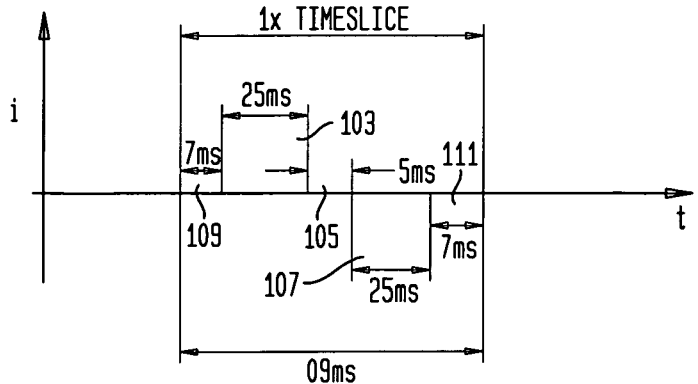
FIG. 3E is a graph of a single stimulation current.

With reference to FIG. 3D there is shown a stimulation sequence via electrode e[B]. It will be noted that stimulation pulse 102 occurs at exactly the same time as stimulation pulse l(a2) of FIG. 3C. Such coincidences occur more and more frequently depending on the number of channels used.

There are at least two problems associated with the above stimulation strategy by which stimulations may be delivered by two or more electrodes simultaneously. Firstly, as discussed above, it is well known that simultaneous, or very near simultaneous, stimulation produces a deterioration in the quality of the sound perceived by the user, due to the interaction of simultaneous current paths between the electrodes.

Consequently the application of stimulations on a number of channels simultaneously is undesirable. A further problem is that simultaneous stimulation requires very substantial processing power and so is not possible in the majority of cochlear implants presently available.

In light of the above problems the inventors have incorporated a preferred refinement for determining which information signals, coming from amplitude detectors 37 and period estimation modules 39 are most appropriate for acting upon in order to produce a high quality percept in a user. According to the invention, for any stimulation period i.e. "timeslice" t0 the signals AMP[A,t0], . . . , AMP[V,t0] are ordered according to magnitude and a stimulation current is generated by means of the electrode which corresponds to the signal AMP[A,t0], . . . , AMP[V,t0] having the greatest magnitude. (It should be noted that, when implanted, electrodes e[A], . . . , e[V] are tonotopically mapped to filters fA, . . . , fV so that electrode e[A] is most apically placed whereas electrode e[v] is most basally placed.) For example, if it is found that AMP[F,t0] has the greatest magnitude at a given timeslice then electrode e[F] is used to deliver the monopolar stimulation in the next timeslice t1.

A further variation to this scheme is that a number of the next largest magnitude signals are also determined in the same timeslot, for example AMP[G,t0]>AMP[B,t0]>AMP[K,t0] might be determined to have the magnitudes next greatest to AMP[F,t0]. In that case those values are assigned to AMP[G,t1], AMP[B,t1] and AMP[K,t1] respectively. During the next timeslice, t1, the procedure is repeated and it may be that AMP[G,t1] is selected as having the greatest magnitude so that electrode e[G] is selected for delivering a stimulation pulse of amplitude corresponding to AMP[G,t1] =AMP[G,t0]. By using this scheme it is possible that signals having a large magnitude, though not the greatest, are presented to the user after a short time delay. The inventors have found that most acoustic power is centred around the lower frequency bands which have longer periods associated with them whereas the higher frequency bands generally have less power associated with them as well as being of shorter period. Accordingly, it is predominantly higher frequency sounds which are delayed rather than lower frequency sounds.

A further refinement is that rather than calculate period estimates in respect of the outputs from filters centred at higher frequencies, for example for filters Fl, . . . , FV period estimators 391, . . . , 39V simply generate a constant signal, or periodicity value, indicating a period of 1.25 ms i.e. a periodicity value towards the highest stimulation rate that the device is capable of supporting.

While the preceding description covers a system utilising period estimators on some or all of the bandpass filtered signals, it is possible to implement the system more simply. A stimulus could be requested each time a positive zero-crossing is detected on a filter output. Once per timeslice each channel is interrogated to see if it has a stimulation request pending. If there are no requests pending, then no action is required. If there is exactly one request pending, then a stimulus is generated corresponding to that request.

If more than one request is pending, then the following actions are taken. The requests are sorted according to the amplitudes of the corresponding bandpass filtered signals. A stimulus is generated corresponding to the bandpass filtered signal with the largest amplitude. The next N largest (preferably 5 largest) amplitude requests are delayed by one timeslice. Any remaining requests are cancelled.

This system is simpler to implement than that previously described. It has two main disadvantages, however. The previously described system utilising period estimates acts to limit the stimulation rate on higher frequency channels. This is directly beneficial in that excessive stimulation with little information content is avoided. More importantly, in the case of relatively large amplitude high frequency signals, the lower frequency signals will be completely lost in the simpler system. The rate-limiting effect of the period-estimation system will mean that the low-frequency signal will always get through.

The request generators 41-A, . . . , 41-V and request arbitrator 43 operate to determine which electrode will be stimulated from the AMP[A], . . . , AMP[V] and PERIOD [A], . . . , PERIOD[V] signals. The operation of the request generators and the request arbitrator, in order to implement the aforedescribed scheme, will now be explained with exemplary reference to request generator 41A.

The AMP[A] and PERIOD[A] signals are inputs to request generator module 41A. Another input to the request generator is the CLK signal which corresponds to the present timeslice. The CLK signal is modulus 256 to avoid overflow problems. The last input to request generator 41A is a command signal ARB_CMD[A] from request arbitrator 43.

The outputs from request generator 41A are TSLICE[A] and REQ_AMP[A].

The TSLICE[A] represents the time at which it is proposed by generator 41A that a stimulation be delivered having an amplitude value represented by REQ_AMP[A].

The relationship between TSLICE[A] and PERIOD[A] and REQ_AMP[A] and AMP[A] is determined by the value of the ARB_CMD[A] signal. The ARB_CMD[A] signal can take one of three values REQUEST, DELAY, DISCARD. When ARB_CMD[A] takes the value:

REQUEST
then REQ_AMP[A]:=AMP[A]; TSLICE[A]:=CLK+PERIOD[A]
DELAY
then TSLICE[A]:=TSLICE[A]+1
DISCARD
take no action.

The principle behind these rules is that in the event that request arbitrator 43, whose operation will shortly be described, determines that a stimulation pulse should be applied corresponding to the output from filter 35A then by sending an ARB_CMD[A] signal having the value REQUEST to request generator 41A the amplitude and timing of the stimulation pulse is made available at the next timeslice. Alternatively, if ARB_CMD[A] takes the value DELAY then the corresponding TSLICE[A] variable is incremented. Construction of the request generator, in order to implement the above rules is readily accomplished according to established synchronous digital design techniques.

Request arbitrator module 43 takes as its input the signals TSLICE[A], . . . , TSLICE[V] from each of the request generators 41A-41V, REQ_AMP[A], . . . , REQ_AMP[V] and the CLK signal. Arbitrator module 43 generates a signal P_CHAN which identifies which of electrodes e[A], . . . , e[V] of the electrode array is to be used to apply a stimulation.

The arbitrator module also generates a signal P_AMP which takes a value REQ_AMP[A], . . . , REQ AMP[V] which is used, after scaling as will subsequently be described, to determine the amplitude of the signal to be used when applying stimulation. Request arbitrator module 43 operates according to the following rules:

1. Find all TSLICE[i] with a value equal to CLK.
2. Find N channels of those determined in Step 1 which have the largest value of REQ_AMP[j]. The channel with the largest value of REQ_AMP[j] and TSLICE[j] as determined in step 1 is found and P_CHAN set to j and P_AMP set to REQ_AMP[j]. So that a stimulation is directed via electrode e[j] with amplitude scaled from the value P_AMP=REQ_AMP[j]. This is accomplished by setting the ARB_CMD[j] signal to REQUEST.
3. The channels having the next N-1 largest amplitude values REQ_AMP[ ] are delayed by one timeslice for consideration during set up for the next stimulation. This is achieved by sending an ARB_CMD[ ] signal to the corresponding N-1 request generators to DELAY.
4. The remaining channels, which were selected in step 1 but not in step 2 are discarded. This is achieved by sending the corresponding request generators an ARB_CMD[ ] signal of value DISCARD.
5. If any of the request generators is sending a specific "no pulse request" then the corresponding ARB_CMD[ ] signals are set to REQUEST.

Once the P_CHAN and P_AMP values have been determined they are passed to Loudness growth function module 47. The growth function module takes into account the predetermined comfort and threshold levels of the user of the cochlear prosthesis in order to map the P_AMP values into the listeners dynamic range. Such mapping is known in the prior art and the reader is referred to U.S. Pat. No. 4,532,930 to the same applicant for further details.

The invention is most conveniently practised, in accordance with the embodiment of FIG. 1, by programming a SPrint speech processor, available from Cochlear Limited of 14 Mars Road, Lane Cove, NSW 2066, Australia, in order to perform the operations described in relation to FIG. 2. The SPrint speech processor is used in conjunction with a CI24M cochlear implant receiver-stimulator from the same vendor.

Figure 4:
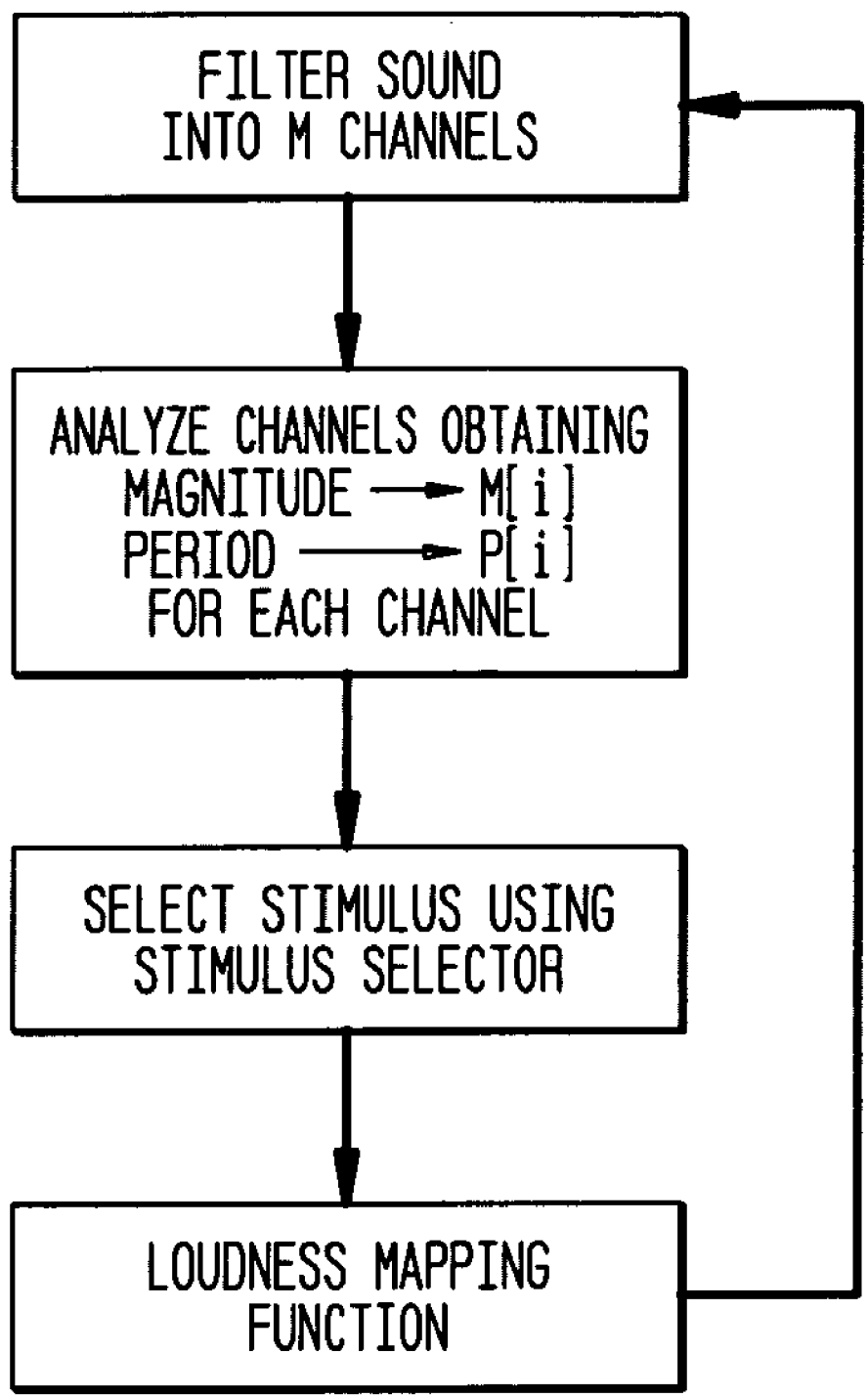
FIG. 4 is a flowchart of procedural steps used in implementing the present invention by means of software on an apparatus of the type depicted in FIG. 1A.

With reference to FIG. 4 there is depicted a block diagram of the overall operational procedure for implementing the present invention in software. At block 201, for each sample period, the sound signal is filtered into the required number of channels. At block 202, the signal in each channel is analysed to determine its amplitude, and the period of the signal. The latter may be performed by determining the time between successive zero crossings, as described above. Based upon the values for the amplitude and period for each channel, block 203 selects which channel signal is to be used as the basis for stimulation, and hence the electrode to be stimulated. Loudness mapping block 204 performs the function of mapping the desired amplitude stimulus within the dynamic range for the selected electrode. The latter step is well known to those skilled in the art.

Figure 5:
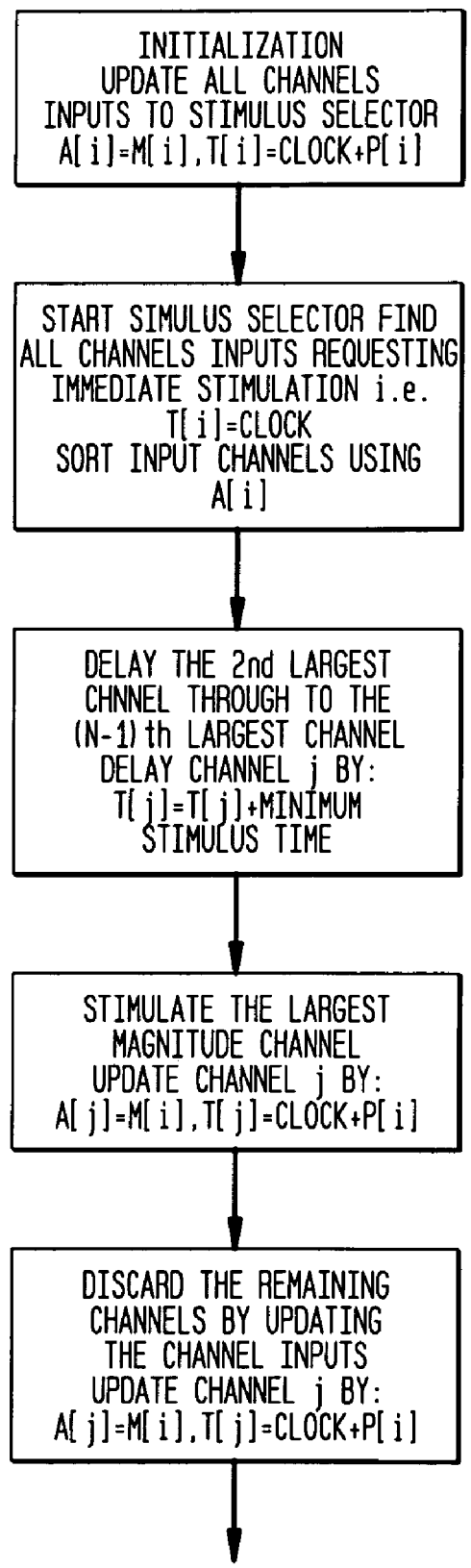
FIG. 5 is a flowchart of procedural sub-steps involved in one of the boxes appearing in FIG. 3.
Figure 1:
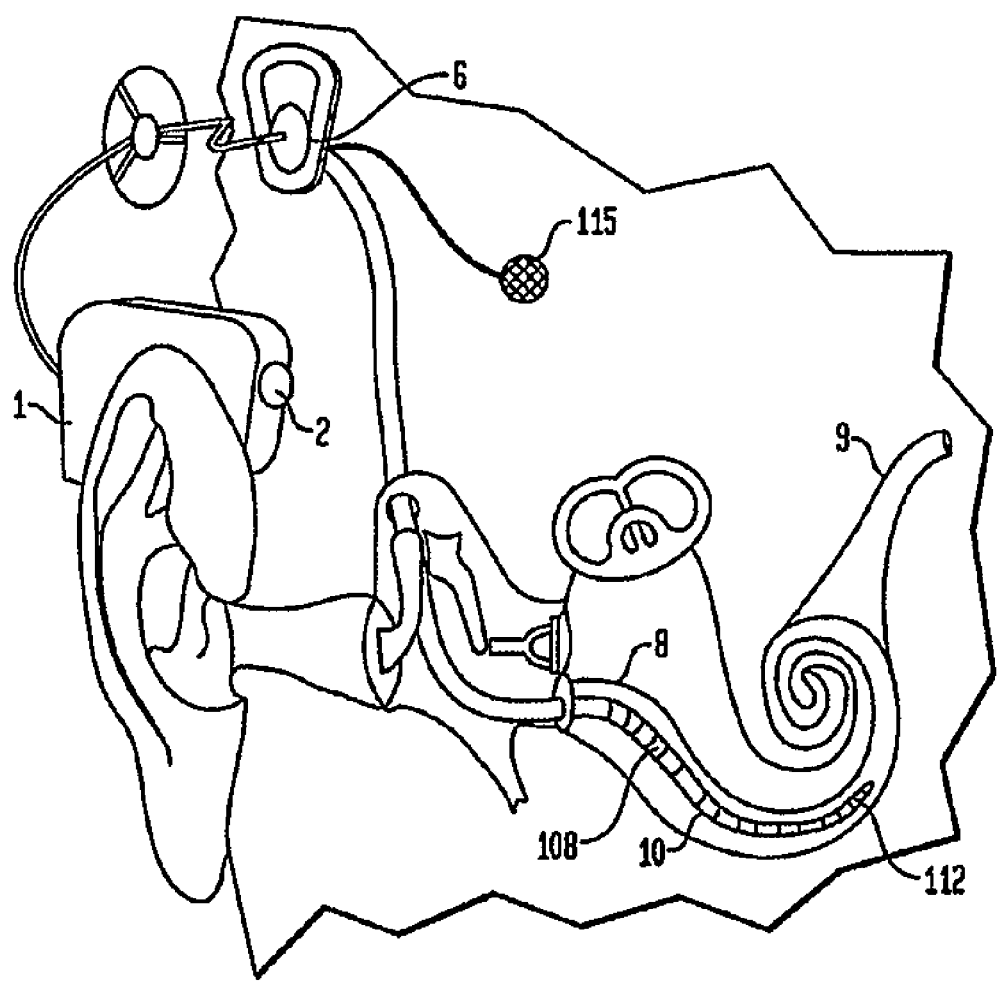
Figure 1A:
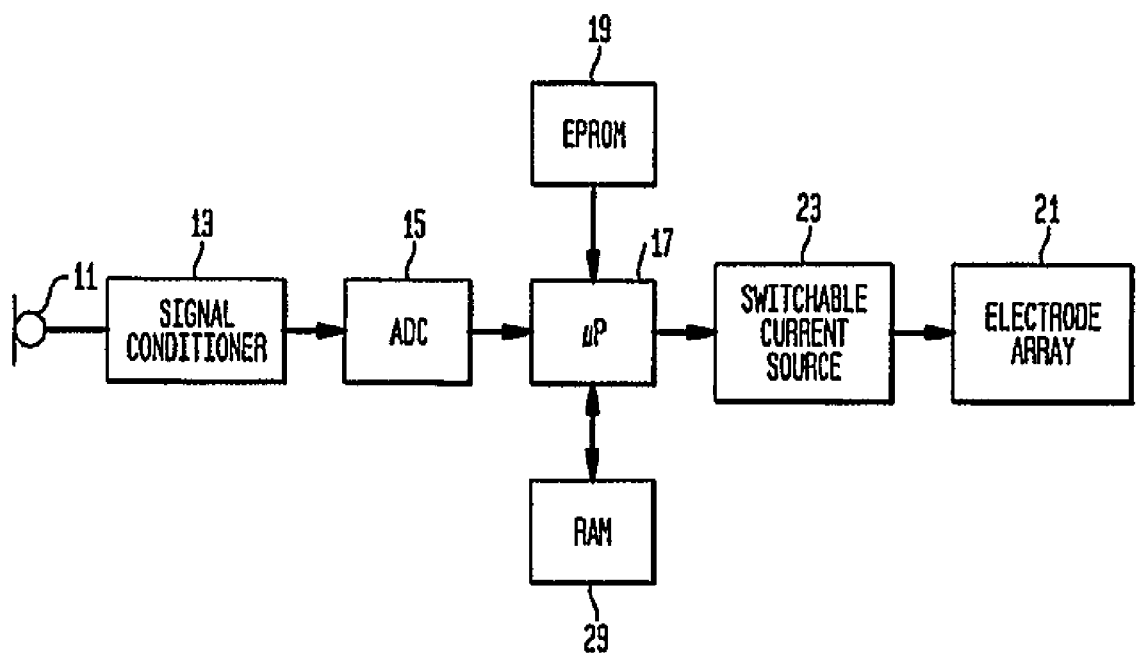
Figure 2:
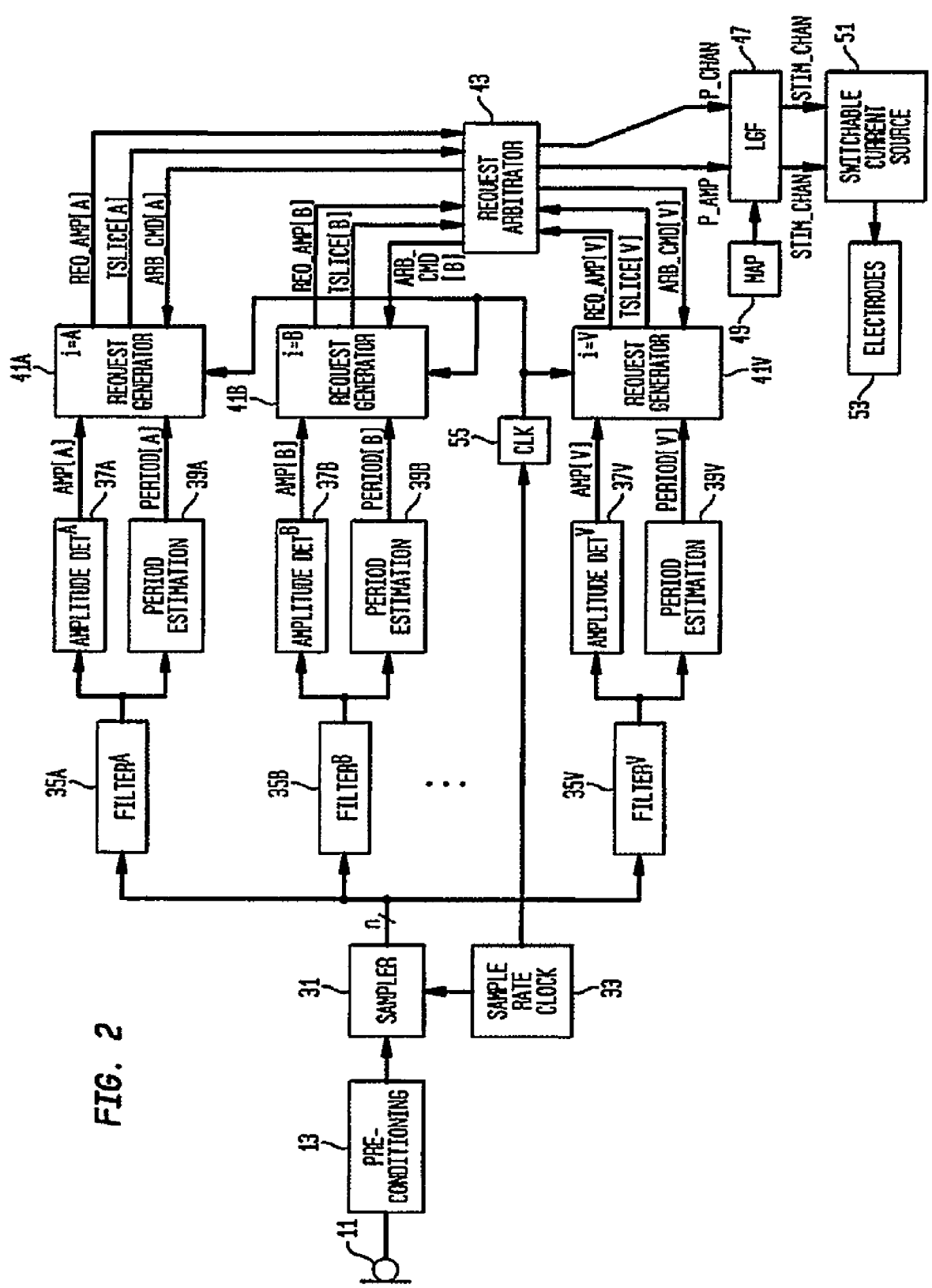
Figure 3A:
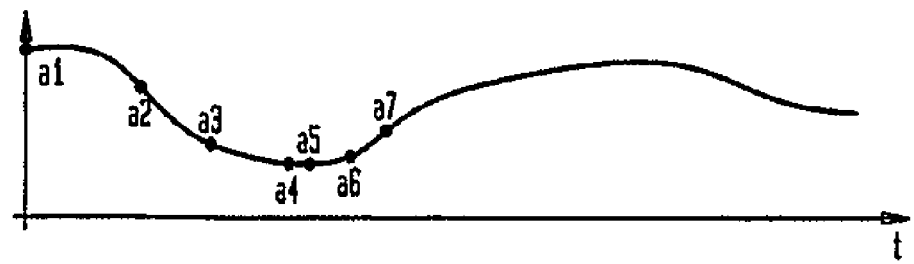
Figure 3B:
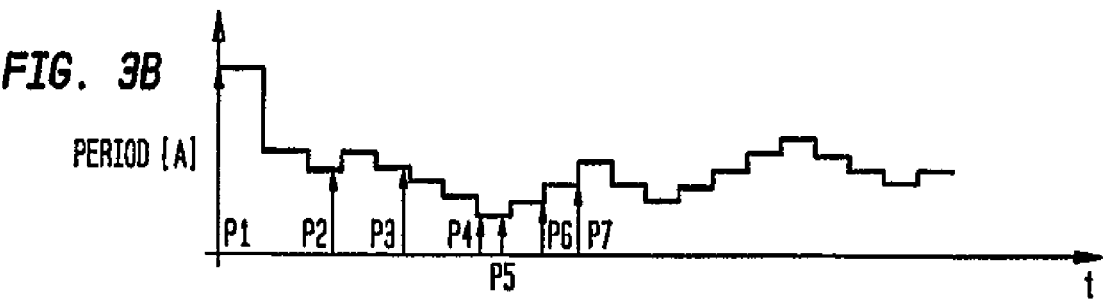
Figure 3C:
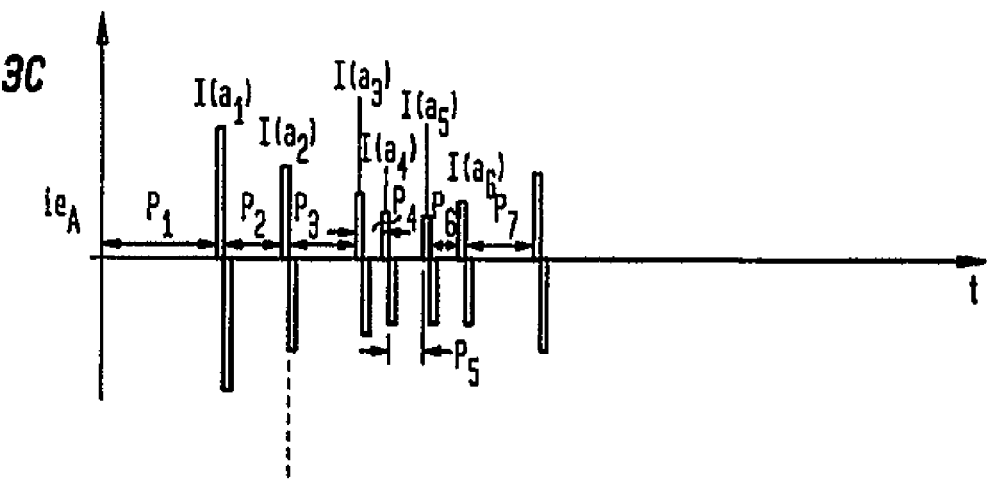
Figure 3D:
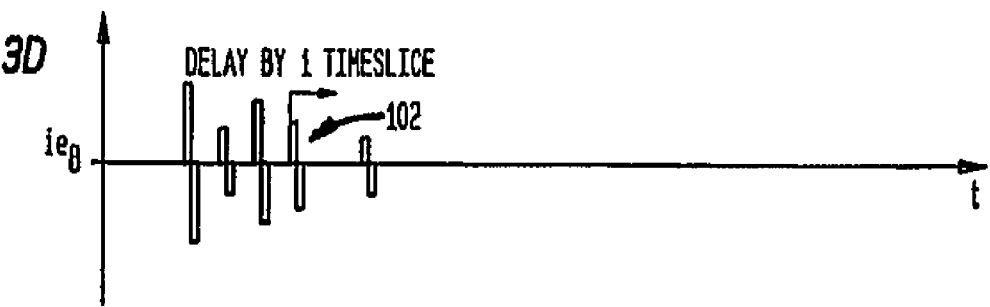
Figure 3E:
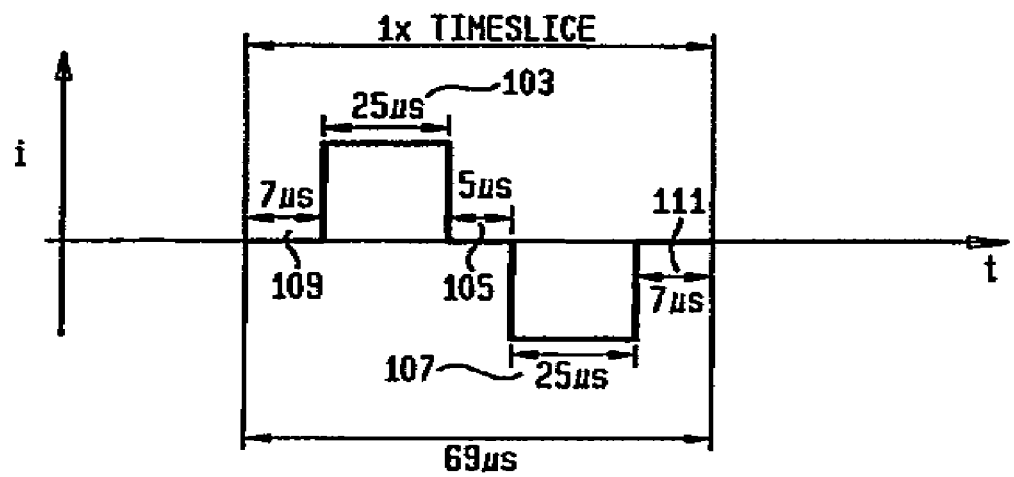
Figure 4:
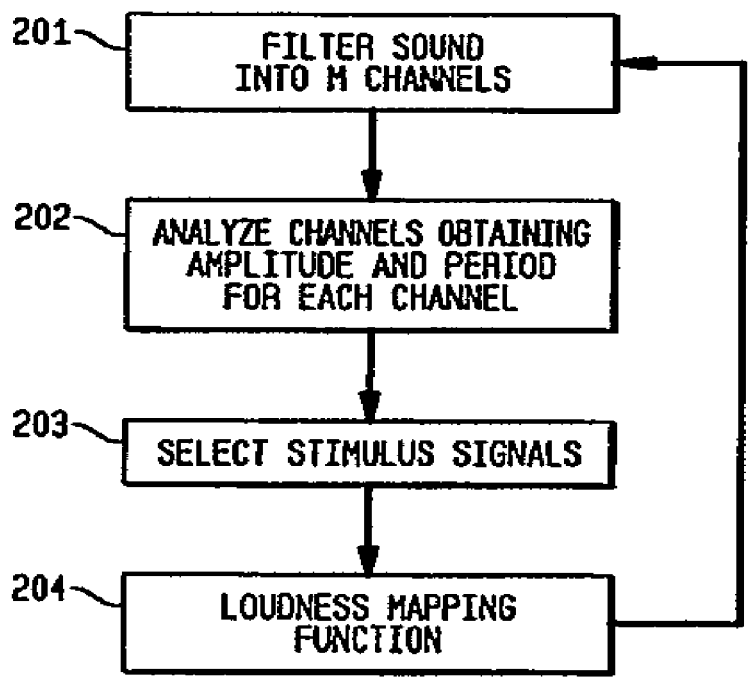
Figure 5:
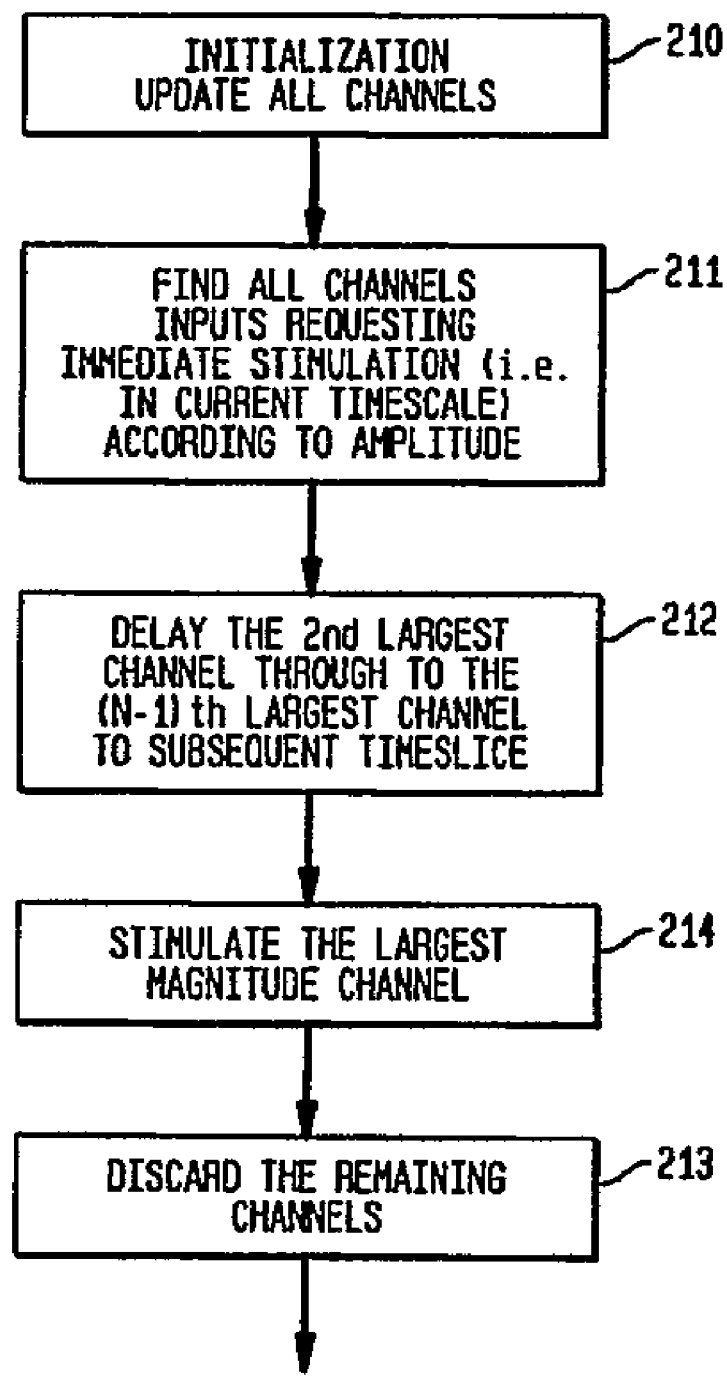

FIG. 5 further details the operational steps performed in box 203 of FIG. 4. At initialisation, in block 210, the stimulus selector updates all inputs. The inputs are the values for amplitude and period as described previously. At block 211, each input channel is checked to determine if a stimulation is being requested for the next period, based upon the period value, and all such channels are sorted according to amplitude. At block 212, all channels but the largest amplitude channel are delayed to a later stimulation period. In block 214, the largest amplitude channel is selected as the basis for stimulation, and the inputs for that channel are updated to reflect that a stimulus will be delivered that period. Block 213 completes the process by discarding the remaining channels by updating their inputs, and returning to the process of block 210 for the next period, time j.

While the invention has been described with reference to preferred embodiments, it is to be understood that these are merely illustrative of the application of principles of the invention. Accordingly, the embodiments described in particular should be considered exemplary, not limiting, with respect to the following claims.

The invention claimed is:

1. A cochlear implant prosthesis of the type having a transducer for converting an acoustic signal to an electrical signal, a plurality of bandpass filtering means responsive to said electrical signal and operatively producing a plurality of bandpass filtered signals, signal processing means responsive to said plurality of bandpass filtered signals and operatively generating stimulation commands, electrode driving means responsive to said stimulation commands and an electrode array coupled to said electrode driving means for operatively delivering to a user of said cochlear implant prosthesis stimulations in accordance with said stimulation commands, said signal processing means including:
   a) period estimation means, responsive to said filtered signals and operatively generating periodicity signals indicative of the periodicity of each of at least a number of said plurality of filtered signals;

b) amplitude estimation means responsive to said filtered signals and operatively generating magnitude signals indicative of the magnitude of each of said plurality of filtered signals;

c) selection means responsive to said magnitude signals arranged to select only one filtered signal of said plurality of filtered signals in each stimulation period, said selection means generating said stimulation commands including a command to stimulate by means of an electrode operatively best corresponding to said one filtered signal, said command to stimulate further specifying a time for stimulation to occur dependent on a corresponding one of said periodicity signals.

2. A cochlear implant prosthesis according to claim 1, wherein said period estimation means operatively determines a value for the time between successive zero crossings by the filtered signal, and responsive to this value generates said periodicity signal.

3. A cochlear implant according to claim 2, wherein said period estimation means is further responsive to previous values of said time between successive zero crossings, so that a smoothed period estimate value is generated, and responsive to this value said period estimation means generates said periodicity signal.

4. A cochlear implant according to claim 3, wherein said periodicity signal is scaled to an integral multiple of the time taken to deliver one stimulation pulse.

5. A cochlear implant according to claim 1, wherein said selection means is responsive to the amplitude and selects said one filtered signal on the basis that said signal has the greatest amplitude.

6. A cochlear implant according to claim 1, wherein the rates of stimulation operatively delivered to each electrode differ tram each other in response to said periodicity signals.

7. A processing device for a cochlear implant prosthesis, said prosthesis being of the type including electrode driving means responsive to stimulation commands and an electrode array coupled to said electrode driving means for operatively delivering to a user of said cochlear implant prosthesis stimulations in accordance with said stimulation commands, said processing device being responsive to a transducer for converting an acoustic signal to an electrical signal and including a plurality of bandpass filtering means responsive to said electrical signal and operatively producing a plurality of bandpass filtered signals, signal processing means responsive to said plurality of bandpass filtered signals and operatively generating stimulation commands, said signal processing means including:

a) period estimation means, responsive to said filtered signals and operatively generating periodicity signals indicative of the periodicity of each of at least a number of said plurality of filtered signals;

b) amplitude estimation means responsive to said bandpass filters operatively generating magnitude signals indicative of the magnitude of each of said plurality of filtered signals;

c) selection means responsive to said magnitude signals arranged to select only one filtered signal of said plurality of filtered signals in each stimulation period, said selection means generating said stimulation commands including a command to stimulate by means of an electrode operatively best corresponding to said filtered signal, said command to stimulate further specifying a time for stimulation to occur dependent on a corresponding one of said periodicity signals.

8. A processing device according to claim 7, wherein said period estimation means operatively determines a value for the time between successive zero crossings by said filtered signal, and responsive to this value generates said periodicity signal.

9. A processing device according to claim 8, wherein said period estimation means is further responsive to previous values of said time between successive zero crossings, so that a smoothed period estimate value is generated, and responsive to this value said period estimation means generates said periodicity signal.

10. A processing device according to claim 9, wherein said periodicity signaf is scaled to an integral multiple of the time taken to deliver one stimulation pulse.

11. A processing device according to claim 7, wherein said selection means is responsive to the amplitude and selects said one filtered signal on the basis that said signal has the greatest amplitude.

12. A processing device according to claim 7, wherein the stimulation commands are such that the rates of stimulation operatively delivered to each electrode differ from each other in response to said periodicity signals.

13. A method of operating a cochlear implant prosthesis of the type including a plurality of bandpass filters each having a characteristic centre frequency, said filters generating a corresponding plurality of filtered signals, said prosthesis further including stimulation delivery means coupled to an electrode array, said method including the steps of:

a) in each of a number of time intervals, determining the amplitude for each of said plurality of filtered signals and a periodicity value for at least some of said plurality of filtered signals;

b) selecting only one of said signals as a basis for stimulation in each stimulation period; and c) applying a stimulation current by means of an electrode of said electrode array tonotopically closest to the centre frequency of the bandpass filter producing the signal determined in step b), said stimulation current being applied during a time interval determined from the periodicity value of the signal determined in step b).

14. A method according to claim 13, wherein said periodicity value is determined by acquiring a period value for the time between successive zero crossings by the filtered signal, and responsive to the period value generating said periodicity signal.

15. A method according to claim 14, wherein said periodicity value is determined using a smoothed period value, said smoothed value being determined in response to current and previous values of said period value, and responsive to said smoothed period value said periodicity signal is generated.

16. A method according to claim 15, wherein said periodicity value is determined for all of said filtered signals.

17. A method according to claim 16, wherein step (b) includes determining which of said plurality of signals has the greatest amplitude.

18. A method according to claim 13, wherein the rates of stimulation operatively delivered to each electrode differ from each other in response to said periodicity signals.

* * * * *

UNITED STATES PATENT AND TRADEMARK OFFICE
CERTIFICATE OF CORRECTION

PATENT NO. : 7,072,717 B1
APPLICATION NO. : 10/030830
DATED : July 4, 2006
INVENTOR(S) : Joe Wolf et al.

It is certified that error appears in the above-identified patent and that said Letters Patent is hereby corrected as shown below:

The title page should be deleted and substitute therefore the attached title page.
In the drawings, Sheet 1, Figure 1 is replaced with the Formal Drawing attached hereto.
In the drawings, Sheet 2, Figure 1A is replaced with the Formal Drawing attached hereto.
In the drawings, Sheet 3, Figure 2 is replaced with the Formal Drawing attached hereto.
In the drawings, Sheet 4, Figure 3A is replaced with the Formal Drawing attached hereto.
In the drawings, Sheet 4, Figure 3B is replaced with the Formal Drawing attached hereto.
In the drawings, Sheet 4, Figure 3C is replaced with the Formal Drawing attached hereto.
In the drawings, Sheet 4, Figure 3D is replaced with the Formal Drawing attached hereto.
In the drawings, Sheet 4, Figure 3E is replaced with the Formal Drawing attached hereto.
In the drawings, Sheet 5, Figure 4 is replaced with the Formal Drawing attached hereto.
In the drawings, Sheet 6, Figure 5 is replaced with the Formal Drawing attached hereto.

Signed and Sealed this

Third Day of April, 2007

JON W. DUDAS
*Director of the United States Patent and Trademark Office*

United States Patent
Wolf et al.

(10) Patent No.: US 7,072,717 B1
(45) Date of Patent: Jul. 4, 2006

(54) MULTIRATE COCHLEAR STIMULATION STRATEGY AND APPARATUS

(75) Inventors: Joe Wolf, Coogee (AU); Paul Michael Carter, Carlingford (AU); Simon Geoffrey Parker, Ryde (AU); Robert Fearn, Maroubra (AU); Niki Frampton, Eastwood (AU)

(73) Assignee: Cochlear Limited, Lane Cove (AU)

( * ) Notice: Subject to any disclaimer, the term of this patent is extended or adjusted under 35 U.S.C. 154(b) by 618 days.

(21) Appl. No.: 10/030,830

(22) PCT Filed: Jul. 13, 2000

(86) PCT No.: PCT/AU00/00838
§ 371 (c)(1),
(2), (4) Date: Jun. 5, 2002

(87) PCT Pub. No.: WO01/03622
PCT Pub. Date: Jan. 18, 2001

(30) Foreign Application Priority Data
Jul. 13, 1999 (AU) .................. PQ1610

(51) Int. Cl.
*A61F 11/04* (2006.01)
*H04R 25/00* (2006.01)
(52) U.S. Cl. .................. 607/57; 381/320
(58) Field of Classification Search .......... 607/55–57, 607/136, 137
See application file for complete search history.

(56) References Cited

U.S. PATENT DOCUMENTS

| | | | |
|---|---|---|---|
| 4,357,497 A | 11/1982 | Hochmair et al. | |
| 4,400,590 A | 8/1983 | Michelson | |
| 4,441,202 A * | 4/1984 | Tong et al. | 381/326 |
| 4,532,930 A | 8/1985 | Crosby et al. | |
| 4,593,696 A * | 6/1986 | Hochmair et al. | 607/57 |
| 5,597,380 A * | 1/1997 | McDermott et al. | 607/57 |
| 5,601,617 A | 2/1997 | Loeb et al. | |
| 5,749,912 A | 5/1998 | Zhang et al. | |
| 5,800,475 A | 9/1998 | Jules | |
| 6,289,247 B1 * | 9/2001 | Faltys et al. | 607/57 |

OTHER PUBLICATIONS

PCT International Search Report for PCT/AU00/00838; filed Jul. 13, 2000; published Jan. 18, 2001 (WO 01/03622 A1).

Technical Manual: The Laura Cochlear Prosthesis, Antwerp Bionic Systems, N.V., 1991.

Peeters, et al., The Laura Cochlear Implant Programmed with the Continuous Interleaved and Phase-Locked Continuous Interleaved Strategies, Cochlear Implants: New Perspectives, 1993.

Kong, Lai Wai, Psychophysical Studies Investigating a Place/Rate Speech Coding Strategy for a Multi-Electrode Cochlear Implant, University of Melbourne, Thesis, Jul. 1990.

* cited by examiner

*Primary Examiner*—George Manuel
*Assistant Examiner*—Nicole R. Kramer
(74) *Attorney, Agent, or Firm*—Jagtiani + Guttag

(57) ABSTRACT

An improved processing approach is disclosed in order to allow for different rates of stimulation to be used for different electrodes in a multi-electrode cochlear implant. When the incoming signal is processed by filter array (35), each channel is processed to determine amplitude (37) and to estimate the period of the signal in that channel (39). The amplitude and period information is used to determine which electrode is stimulated, and the timing of that stimulation.

18 Claims, 6 Drawing Sheets